United States Patent
Saptari et al.

(10) Patent No.: US 7,099,003 B2
(45) Date of Patent: Aug. 29, 2006

(54) SPECTROSCOPIC SYSTEMS AND METHODS

(75) Inventors: Vidi A. Saptari, Chelsea, MA (US); Kamal Youcef-Toumi, Cambridge, MA (US)

(73) Assignee: Delta Search Labs, Inc., Cambridge, MA (US)

( * ) Notice: Subject to any disclaimer, the term of this patent is extended or adjusted under 35 U.S.C. 154(b) by 0 days.

(21) Appl. No.: 10/840,686

(22) Filed: May 6, 2004

(65) Prior Publication Data

US 2005/0012925 A1   Jan. 20, 2005

Related U.S. Application Data

(60) Provisional application No. 60/469,171, filed on May 9, 2003.

(51) Int. Cl.
*G01J 3/42* (2006.01)
*G01N 21/25* (2006.01)

(52) U.S. Cl. .................. 356/319; 356/328; 356/418

(58) Field of Classification Search ........ 356/326–330, 356/331, 332, 416–419, 308, 306, 309, 319; 250/339.01, 339.11, 339.12; 702/94, 117
See application file for complete search history.

(56) References Cited

U.S. PATENT DOCUMENTS

| | | | | |
|---|---|---|---|---|
| 2,834,246 A | * | 5/1958 | Foskett et al. | 356/418 |
| 4,040,747 A | | 8/1977 | Webster | 356/188 |
| 4,064,535 A | * | 12/1977 | Cross et al. | 348/164 |
| 4,070,111 A | | 1/1978 | Harrick | 356/83 |
| 4,090,792 A | * | 5/1978 | Bunge | 356/418 |
| 4,804,266 A | | 2/1989 | Barshad | 356/308 |
| 4,804,271 A | * | 2/1989 | Cammann | 356/416 |
| 5,063,528 A | * | 11/1991 | Miwa et al. | 702/150 |
| 5,070,245 A | * | 12/1991 | Rantala et al. | 250/343 |
| 5,231,462 A | * | 7/1993 | Dschen | 356/328 |
| 5,268,745 A | * | 12/1993 | Goody | 356/418 |
| 5,774,213 A | * | 6/1998 | Trebino et al. | 356/320 |
| 5,852,498 A | | 12/1998 | Youvan et al. | 356/417 |

FOREIGN PATENT DOCUMENTS

JP    11-037842    * 2/1999

OTHER PUBLICATIONS

Scheer, J., *Applied Optics*, 26(15):3077-3082 (1987).
International Search Report for PCT/US2004/014253, mailed Dec. 8, 2004.

* cited by examiner

*Primary Examiner*—Layla G. Lauchman
(74) *Attorney, Agent, or Firm*—Mintz, Levin, Cohn, Ferris, Glovsky and Popeo, P.C.

(57) ABSTRACT

The present invention relates to spectroscopic methods and systems for collecting electromagnetic radiation from an object using a continuously-spinning wavelength-selecting (CSWS) device, e.g., an interference filter(s) or grating. One embodiment of the invention provides a spectroscopic system for collecting electromagnetic radiation from a target. The spectroscopic system has at least one beam of electromagnetic radiation that interacts with the target. The system includes a continuously spinning wavelength-selecting (CSWS) device, e.g., a continuously spinning interference filter/grating driven by a DC motor, in the path of the at least one beam. The device filters the radiation with regard to wavelength to produce filtered radiation. The system further includes at least one detector in the path of the at least one beam for detecting the filtered radiation.

28 Claims, 5 Drawing Sheets

(a)    (b)

Trigger signal (once per revolution)

SPECTROSCOPIC SYSTEMS AND METHODS

RELATED APPLICATIONS

This application claims priority to, and the benefit of, earlier filed U.S. Provisional Application Ser. No. 60/469,171, filed May 9, 2003, entitled "SPECTROSCOPIC SYSTEM WITH CONTINUOUSLY-SPINNING WAVELENGTH-SELECTING DEVICE."

BACKGROUND OF THE INVENTION

This invention relates to a spectroscopic system having an improved spectral signal-to-noise ratio and a simpler configuration involving fewer mechanical parts than current grating-based instruments.

At a minimum, a spectrometer (e.g., a Raman, fluorescence, absorption or reflectance spectrometer) includes a light source, a photo-detector and a wavelength-selecting device. A wavelength-selecting device is often called a spectroscope. Depending on the application, the sample can be inserted between the source and the spectroscope or between the spectroscope and the detector.

There are different types of spectrometers. One type of spectrometer is a wavelength-scanning instrument. A wavelength-scanning instrument acquires one wavelength band at any given time. Examples of this type of device are monochromators, tunable interference filters (tunable through various techniques such as mechanical tilting, thermal variation, and opto-acoustical variation) and discrete-filters-spinning-wheel instruments. A discrete-filters-spinning-wheel instrument includes a wheel with a number of discrete filters. The wheel is oriented substantially perpendicular to the path of an optical beam so that the axis of rotation of the wheel is substantially parallel to the optical beam and so that by rotating the wheel one can alternately bring each of the discrete filters into the path of the optical beam. In other words, only one of the discrete narrow bandpass filters is in the path of the light beam at a time.

There are two common methods of sampling and acquiring a radiation signal using a monochromator and at least one of these two common methods is also applicable to tunable interference filters and discrete-filters-spinning-wheel instruments. The first method, termed continuous-scan, controls the wavelength-selecting device to continuously vary the output wavelength. In a monochromator-based instrument, for example, the continuous-scan method smoothly varies the grating angle as a function of time. The continuous-scan method acquires and digitizes the signal while the grating is rotating. One usually performs a rotation cycle, i.e., a cycle involving moving a grating through the grating's range of motion (less than 90 degrees), a number of times. One then averages the acquired data to improve the resulting signal-to-noise ratio. In other words, such a monochromator-based system needs to slow down the rotation of the grating, bring the grating to a stop and start rotating the grating in the opposite direction and the system typically needs to repeat this process many times.

The second method, termed step-and-scan, rotates the grating/filter (in a tilt-tuned instrument) step-wise to a new location and lets the grating/filter settle before starting data acquisition. The method integrates (averages) the signal while the grating is at rest.

Current wavelength-selecting devices, such as monochromators, have some inherent drawbacks:

1. Measurements are usually slow. The inertia of the moving parts (gratings, gear-reduction mechanisms, etc) usually limits the speed of rotation of the moving parts. For the continuous scan method, significant delay occurs as a result of the need to let the grating or filter come to a stop and start moving in the opposite direction with precision and without causing large vibrations. For the step-scan method, significant delay occurs as a result of the need to let the grating or filter settle to within a certain permissible angular window before starting data acquisition.
2. For monochromator and tilting filter instruments, the precision of the rotary stage at least partially determines wavelength repeatability. The rotary stage of such instruments is typically not precise enough for most high-SNR or low-noise applications, requiring high spectral repeatability such as quantitative spectroscopy measurements Other scanning systems (e.g., thermal and opto-acoustic systems) have their own inherent limitations in regard to their ability to reliably and accurately reproduce a specified wavelength.
3. Systems designed for high SNR applications are expensive due to a need for high-precision mechanical and electrical components.
4. Current wavelength-selecting systems are highly sensitive to mechanical vibrations.

For applications requiring high SNR(i.e., most applications today, especially quantitative applications), one typically employs modulation and bandwidth-narrowing techniques. These techniques commonly involve modulating the radiation signal so that one can apply electrical bandwidth-narrowing techniques, such as band-pass filtering and phase-locking techniques, to the resulting signal.

To expand on this last point, in a grating-based spectrometer that does not use modulation, one can tilt the grating to select a particular narrow band of wavelengths and then one integrates the signal over time. Such a method has the disadvantage that the sources of noise regardless of their respective frequencies add on to the resulting signal, negatively impacting the signal-to-noise ratio (SNR). However, by applying modulation at a frequency distinct from the frequencies of most sources of noise, one can increase the resulting SNR.

Spectroscopy practitioners commonly use a mechanical chopper to modulate the radiation arriving at the photo-detector. A mechanical chopper works by mechanically "chopping" (or blocking) the beam path periodically at a predetermined frequency.

Light modulation using such a device has some disadvantages:

1. A mechanical chopper adds complexity to a spectroscopic system. Besides the chopper wheel itself (and other components needed to support rotation of the wheel), the device needs its own electromechanical and electrical components to drive and control the rotation of the chopper wheel and to synchronize the chopper wheel with an associated wavelength-selecting instrument. Thus, modulation using a mechanical chopper can add significant cost to a spectroscopic system.
2. Mechanical choppers are typically bulky and difficult to miniaturize.
3. Measurement becomes slower, because the wavelength-scanning device needs to "wait" for the light chopper to produce enough turns/modulations before proceeding to the next wavelength segment. The slower the modulation frequency, the longer the mechanical-chopper-modulated system needs to obtain a given number of signals. This type of chopping device is usually limited to only a few hundred hertz.

4. Modulation using a mechanical chopper does not eliminate the low frequency (close to DC frequency) stability error, such as those caused by temperature variations or power drifts.

Thus, a need remains for inexpensive spectroscopic systems that have an improved spectral signal-to-noise ratio and a simpler configuration involving fewer mechanical parts than current grating-based instruments.

SUMMARY OF THE INVENTION

The present invention relates to spectroscopic methods and systems for collecting electromagnetic (EM) radiation form a target using a continuously-spinning wavelength-selecting (CSWS) device, e.g., an interference filter or grating. One embodiment of the invention provides a spectroscopic system for collecting EM radiation from a target. The spectroscopic system has at least one beam of EM radiation that interacts with the target. The system includes a continuously spinning wavelength-selecting (CSWS) device, e.g., a continuously spinning interference filter or grating driven by a DC motor, in the path of the at least one beam of EM radiation. The device filters the radiation with regard to wavelength to produce filtered (transmitted or reflected) radiation. The system further includes at least one detector in the path of the at least one beam for detecting the filtered radiation. For present purposes, the EM radiation transmitted by an interference filter or reflected by a grating or emitted by a combination of such elements is referred to as filtered radiation.

In one embodiment, the CSWS device includes a motor and a filter coupled to the motor. The filter spins about an axis that is substantially perpendicular to the primary beam. The system can further include a position encoder coupled to the device and operative to determine the rotational position of the filter. The encoder can determine the rotational speed of the filter and provide digital pulses with a frequency proportional to the rotational speed of the filter. The system can further include a frequency to voltage (F/V) converter in communication with the encoder. The F/V converter receives the digital pulses and provides a feedback voltage proportional to the frequency of the digital pulses. The system can further include a voltage comparison circuit in communication with the F/V converter. The voltage comparison circuit receives a command voltage and the feedback voltage, compares the command voltage and the feedback voltage and regulates the rotational speed of the motor based on the comparison.

Another embodiment of the invention provides a spectroscopic method for collecting EM radiation from a target that interacts with at least one beam of EM radiation. The method includes: filtering the at least one beam using a CSWS device to produce filtered radiation; and detecting the filtered radiation.

In one embodiment, filtering the beam using a CSWS device includes spinning the device about an axis that is substantially perpendicular to the beam. The device can include a motor; and a filter coupled to motor. Thus, the filter spins about an axis that is substantially perpendicular to the primary beam. The method can include using a position encoder to determine the rotational position of the filter. In addition, the method can include using the encoder to determine the rotational speed of the filter and to provide digital pulses with a frequency proportional to the rotational speed of the filter. The method can further include: providing a F/V converter in communication with the encoder; using the F/V converter to receive the digital pulses and to provide a feedback voltage proportional to the frequency of the digital pulses; providing a voltage comparison circuit in communication with the F/V converter; and using the voltage comparison circuit to receive a command voltage and the feedback voltage, to compare the command voltage and the feedback voltage and to regulate the rotational speed of the motor based on the comparison.

BRIEF DESCRIPTION OF THE ILLUSTRATED EMBODIMENTS

Figure 1:
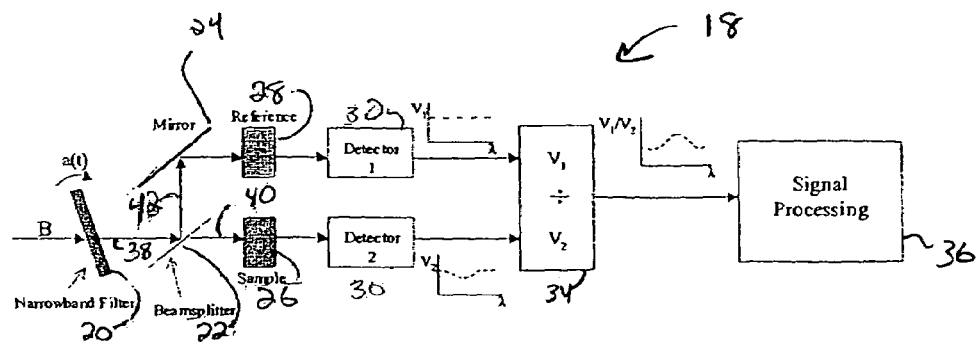
FIG. 1 is a schematic illustration of one embodiment of a spectroscopic system according to the invention.
Figure 3:
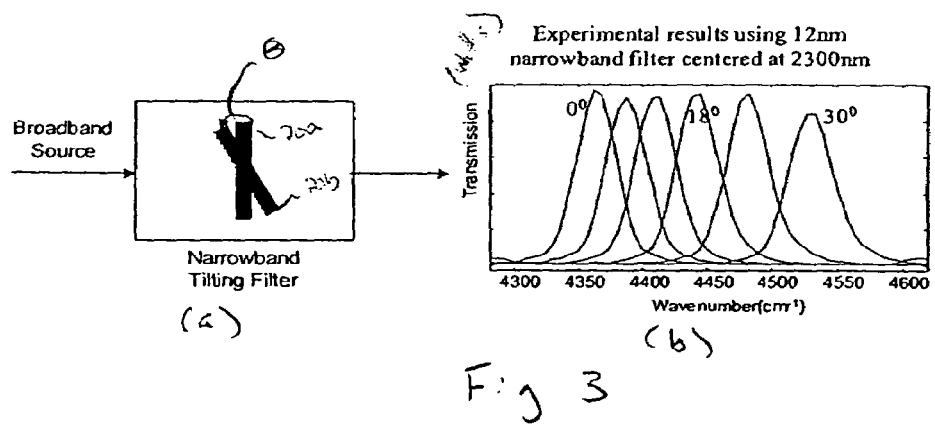
FIG. 3A illustrates one embodiment of a narrowband tilting filter for use with the system of FIG. 1.
Figure 4:
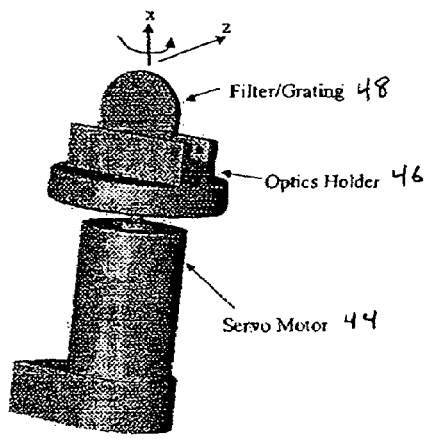
Figure 5:
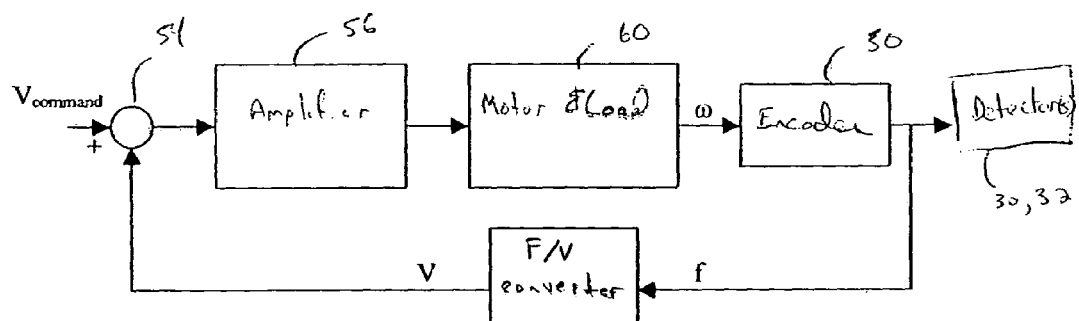
Figure 6:
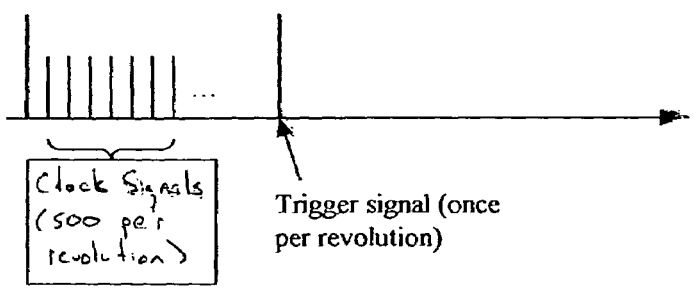
Figure 7:
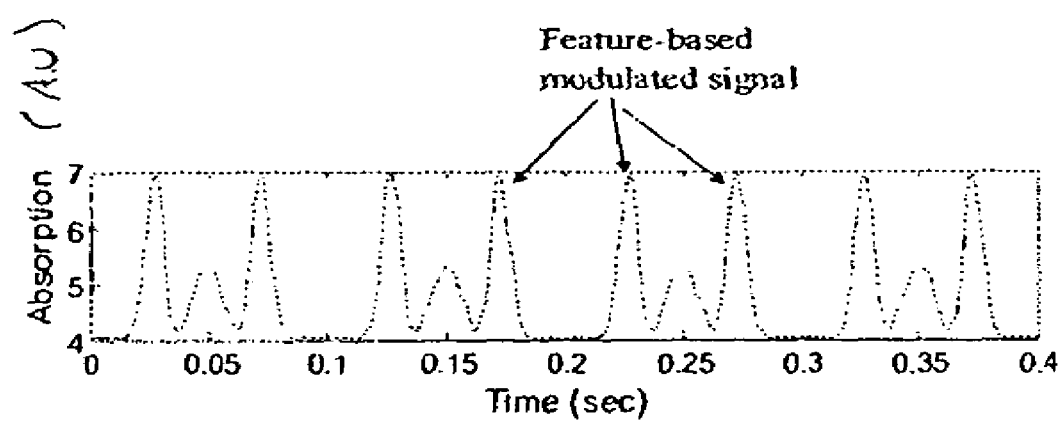
Figure 8:
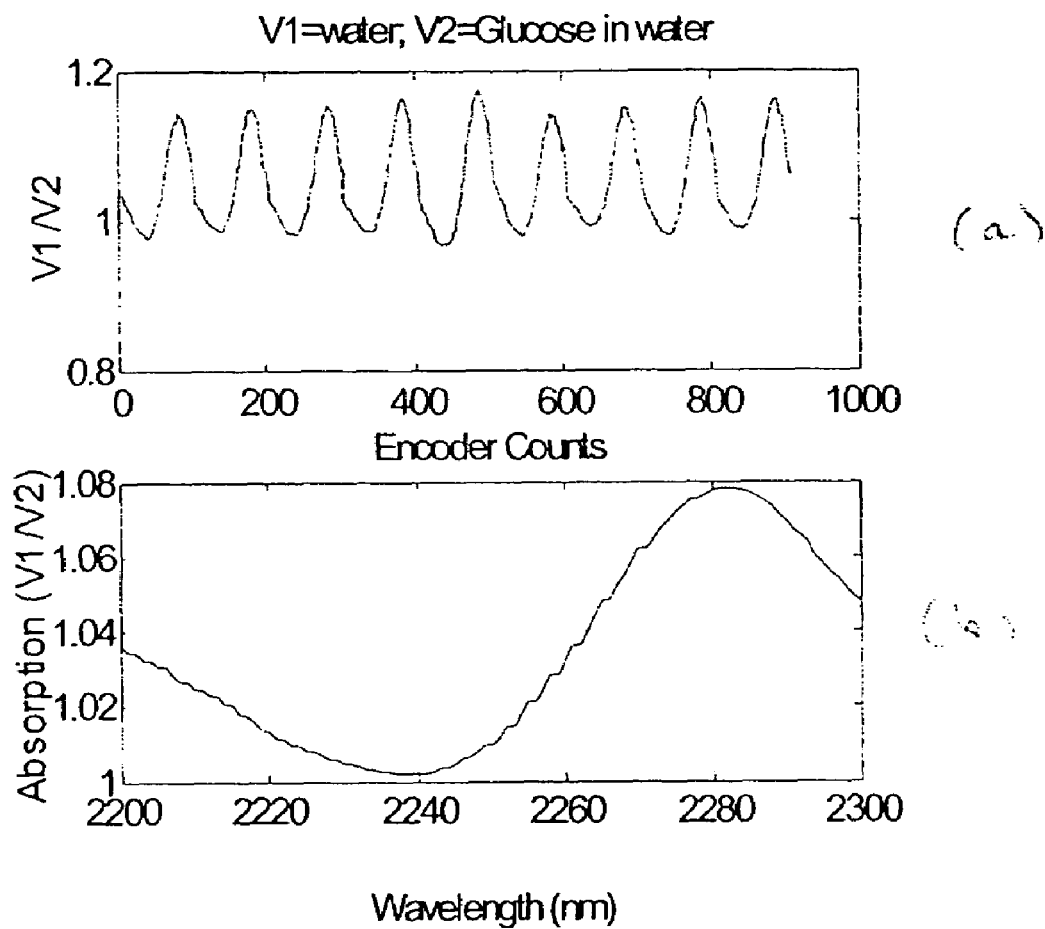
Figure 9:
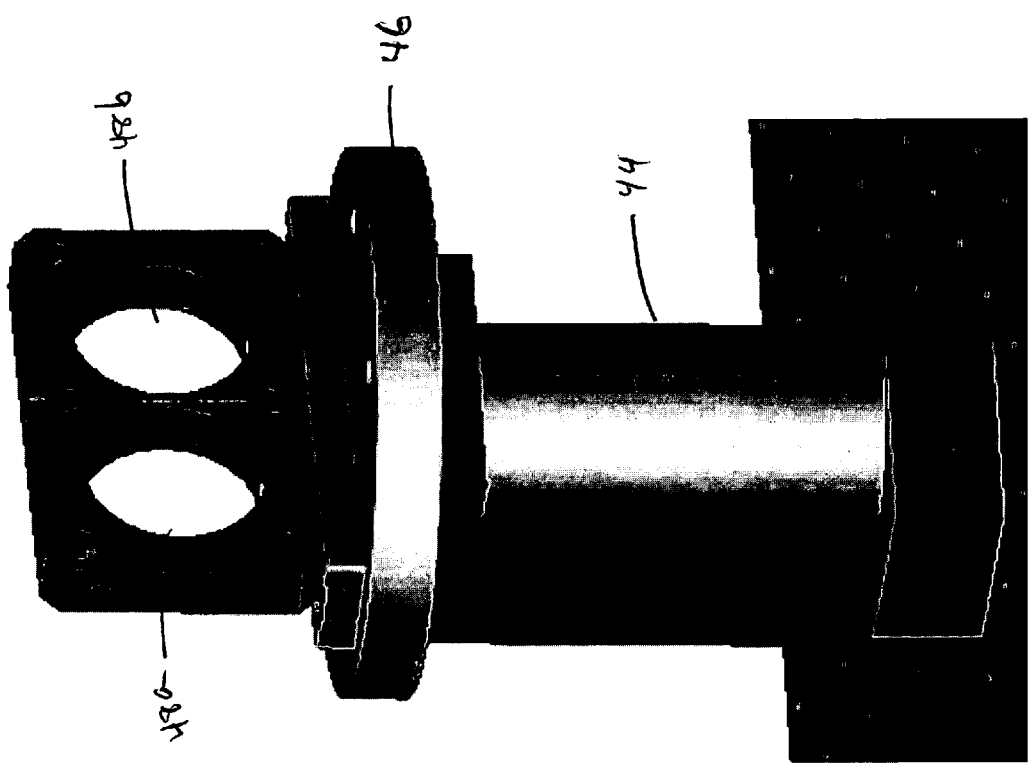

FIG. 3B qualitatively illustrates relative transmission versus wavenumber for a 12 nm narrowband filter centered at 2300 nm;

FIG. 4 illustrates one embodiment of a continuously-spinning wavelength-selecting (CSWS) device for use with the system of FIG. 1;

FIG. 5 illustrates a velocity control system for controlling the rotational velocity of the continuously-spinning wavelength-selecting device of FIG. 1;

FIG. 6 illustrates clock signals provided by the position encoder of FIG. 5 to the data acquisition portion of the system of FIG. 1, the clock signals being displayed as a function of time;

FIG. 7 shows simulated results that one might obtain using the system of FIG. 1, the simulated results showing absorption of radiation by a sample as a function of time;

FIG. 8A shows experimental results obtained using a system similar to the embodiment shown in FIG. 1;

FIG. 8B shows the experimental results of FIG. 8A after post-processing; and FIG. 9 is an alternative embodiment of the CSWS device of FIG. 4.

DETAILED DESCRIPTION OF THE INVENTION

The present invention relates to spectroscopic methods and systems for collecting electromagnetic (EM) radiation from an object using a continuously-spinning wavelength-selecting (CSWS) device, e.g., an interference filter or grating. In the present context, continuously-spinning refers to a device that spins for more than one rotation and a wavelength-selecting device refers to a device that selects a narrow portion of the electromagnetic spectrum.

With reference to FIG. 1, one embodiment of the invention provides a spectroscopic system 18 including a CSWS device 20. The CSWS device 20 interacts with a beam B of EM radiation provided by a source of broadband EM radiation. The CSWS device 20 rotates about an axis that lies in a plane that is substantially perpendicular to the beam B. In other words, setting the z axis as parallel to the beam B, the CSWS device 20 rotates about an axis that is substantially parallel to the x-y plane.

The illustrated embodiment of the spectroscopic system 18 further includes a beamsplitter 22, a mirror 24, sample/target 26 and reference 28 cells, first 30 and second 32 detectors, analog circuitry 34 and signal processor 36. The CSWS device 20 passes a portion 38 of the beam B having a narrow range of wavelengths to the beamsplitter 22. The beamsplitter 22 divides the portion 38 of the beam B into a first subordinate beam 40 and a second subordinate beam 42. The first subordinate beam 40 interacts with the sample cell 26 and then the first detector 30 detects at least a portion of the first subordinate beam 40. Similarly, the second subordinate beam reflects off mirror 24 and interacts with reference cell 28 and then the second detector 32 detects at least a portion of the second subordinate beam 42.

The first and second detectors 30, 32 convert first and second radiation signals to first and second electrical signals, respectively. One embodiment can include analog circuitry 34 to process the first and second electrical signals. The circuitry 34 can apply at least one of a variety of operations, such as division, subtraction and/or addition, to the first and/or second electrical signals as is appropriate for the particular type of measurement one is attempting to obtain. In addition, the analog circuitry can amplify and/or filter the first and/or second electrical signals. An analog-to-digital (A/D) converter (not shown) captures and digitizes the resulting signal. A personal computer or micro-processor 36 then processes the digitized signal and software associated with the personal computer or micro-processor can report results based on the processed digital signal.

Figure 2:
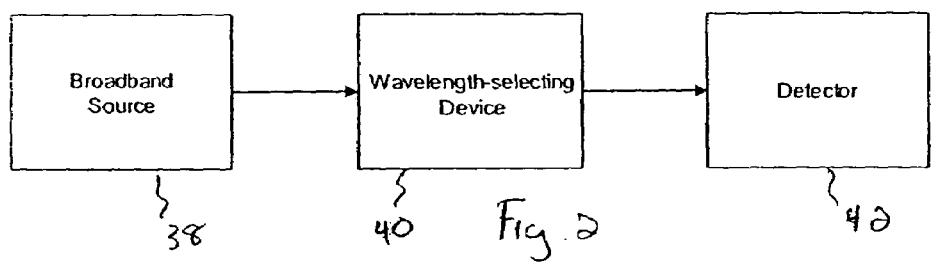
FIG. 2 illustrates basic components of a spectroscopic system such as the system of FIG. 1.

With reference to FIG. 2, basic components of a spectroscopic system such as the system of FIG. 1 include a broadband source of EM radiation 38, a wavelength-selecting (WS) device 40 and a detector 42. One can insert the target object, e.g., a sample, between the source 38 and the WS device 40 or between the WS device 40 and the detector 42.

With reference to FIGS. 1, 3A and 3B, in one embodiment, the CSWS device 20 can include a narrowband spinning interference filter. In FIG. 3A, the spinning filter is shown in a first position 20a, in which the filter is substantially perpendicular to an EM beam coming from a broadband source, and in a second position 20b in which the filter is tilted at an angle θ relative to the first position. The narrow band of wavelengths that an interference filter transmits along a path aligned with the incident beam is a function of the tilt angle of the interference filter. FIG. 3B is a graph providing a qualitative illustration of this phenomenon in the context of a 12 nm narrowband filter centered at 2300 nm. The y axis is linear and the graph is qualitative in that it does not specify transmission values. With reference to FIG. 3B, one can see that the narrow band of wavenumbers, and by implication wavelengths, that the filter transmits depends on the tilt angle. For example, at 0 degrees tilt angle, the peak of the relative transmission along a path aligned with the incident beam occurs at a wavenumber of about 4350 1/cm with a full width at half maximum (FWHM) of about 50 1/cm. While at 30 degrees tilt angle, the peak of the relative transmission occurs at a wavenumber of about 4525 1/cm with a FWHM of about 60 1/cm.

With reference to FIGS. 1 and 4, one embodiment of a CSWS device 20 includes a servo motor 44, an optics holder 46 coupled to the servo motor, and a filter/grating 48 positioned within the optics holder 46. The servo motor can be a DC motor with a direct-drive configuration and can contain a position encoder, e.g., an integrated optical position encoder.

One can use feedback control to control the rotational velocity of the motor. In one embodiment, the motor provides a velocity feedback signal. One can use a tachometer to directly measure the rotational velocity. Alternatively, one can use signals provided by the position encoder to derive a velocity feedback signal.

With reference to FIGS. 4 and 5, one embodiment of a velocity control system for controlling the rotational velocity of the CSWS device of FIG. 1 includes an encoder 50 having a first output coupled to an input of a frequency-to-voltage (F/V) converter 52. The F/V converter 52 has an output coupled to a first input of a voltage comparison circuit 54. The voltage comparison circuit 54 has a second input for receiving a command voltage and an output coupled to an input of an amplifier 56. The amplifier 56 has an output coupled to an input of a motor, e.g., the servo motor 44, that controls the rotational velocity of the motor and its associated load 60 (e.g., filter 48 and holder 46).

Given that the motor and load 60 rotate at a rotational speed ω, the encoder produces digital pulses with a frequency f proportional to ω. An analog frequency-to-voltage converter (LM2907) produces a voltage V proportional to the input pulses' frequency. The voltage comparison circuit 54 compares the voltage produced by the F/V converter with the commanded voltage $V_{command}$ to regulate or control the rotational speed of the motor and load 60, e.g., in one embodiment if $V_{command} - V_{feedback}$ is positive and relatively large, the signal to the motor to increase speed is also relatively large.

In alternative embodiments one may use more elaborate/advanced speed control systems. However, one can also use the position encoder to provide data clocking in real-time to reduce the need for precise control of the rotational velocity of the CSWS device, e.g., of the filter and optical holder.

More specifically, and with reference to FIGS. 5 and 6, when performing data acquisition clocking, one can use the position encoder 50, which provides a number of, e.g., 500, position signals per revolution to clock data acquisition. In other words, with reference to FIGS. 1, 5, and 6, the output of the encoder 50 can couple to the first and second detectors 30, 32 and/or the analog circuitry 34 to provide clock signals for the recording of detection signals. As spectral response of the filter is a function of the filter angle, and the data acquisition "timing" is directly synchronized with position signals representative of filter angle, velocity errors or variations typically associated with the velocity control system of FIG. 5 generally do not cause large measurement errors relative to other sources of error. Once each revolution, a trigger signal starts data acquisition. One can use an encoder index signal, which occurs once per rotation, as the trigger signal.

In one embodiment, the filter/grating device of FIG. 4 is a two sided interference filter that functions as an interference filter when broadband EM radiation is incident on either side of the filter. If the angle of incidence is defined by setting normal incidence as the zero angle, the usable angles of the interference filter is typically about 50 degrees centered on the zero angle. In other words, about 50 degrees of the 180 degrees of rotation per each side of the two-sided interference filter provides usable data, the rest of the rotation providing a discontinuity in the data collection. Another embodiment uses an interference grating having only one operative side and about 50 degrees of the 360-degree rotation provides usable data.

More generally, the CSWS device 20 of FIG. 1 can be a combination of filter(s) and/or grating(s) where at least one of the filter(s) or grating(s) continuously spins to achieve wavelength scanning. For example, with reference to FIG. 9 if one wants to achieve specific spectral windows, e.g., 1500 to 1600 nm and 2200 and 2300 nm, one can combine two narrowband filters side-by-side in locations 48a and 48b, i.e., one for 1500–1600 nm and the other for 2200–2300 nm, and the system can continuously spin the combined filter structure.

With reference to FIG. 7, embodiments of the present invention provide signal modulation with respect to time. FIG. 7 shows a simulation of results that one might obtain using the system of FIG. 1. The simulated results show radiation absorption by a sample/target cell (in absorption units) versus time (in seconds). The simulated results provide a feature-based modulated signal.

As noted above, for applications requiring high SNR or low noise, one typically employs modulation and bandwidth-narrowing techniques. One can modulate the radiation signal so that one can apply conventional electrical bandwidth-narrowing techniques, such as band-pass filtering and phase-locking, e.g., using a phase-locked loop.

Spectroscopy practitioners commonly use a mechanical chopper to modulate the radiation arriving at a photo-detector. Using a CSWS device according to embodiments of the invention instead of a mechanical chopper provides a number of advantages including the following modulation related advantages:

1. As the CSWS device (e.g., a filter or grating) rotates, the recorded radiation signal is naturally modulated. The modulation frequency is determined by the rotation speed of the CSWS device and is therefore typically high relative to frequencies associated with most sources of noise. Many sources of noise such as temperature drift of the sample cell have a relatively low frequency. The characteristics of the "pulses" (such as sinusoidal or Gaussian or Lorentzian) are determined by the absorbing or emitting sample.
2. Signal processing algorithms can be directly applied to the modulated signal.

Modulation using a CSWS is a one-step process. Embodiments of the invention do not need additional modulating hardware or schemes. With the spinning filter modulation technique, at the completion of one revolution, an embodiment of the invention assesses the whole spectral range provided by the CSWS device. The system can take ~$1/100^{th}$ of a second to complete a revolution, depending on the speed of rotation of the filter/grating. For example, in one embodiment, if the rotational speed is 6000 revolutions per minute (RPM), i.e., 100 revolutions per second, then each revolution takes $1/100$ of a second. Letting the system run for a few seconds, and collecting the data improves the SNR as a result of an averaging process. Hence one can perform data processing in "real-time". The revolutions per minute (RPM) of the filter/grating can range, depending on the quality of the motor (e.g., the quality of the bearing within the motor), from about 2,000 RPM to about 30,000 RPM.

For example, using a DC motor model #8324S005 available from Pittman of Pennsylvania, USA, the maximum speed is limited to about 10,000 RPM; sufficient for most applications. With this rotation speed, 166.7 spectral scans are done in one second (10,000 RPM/60 sec per min). Averaging 400 spectra is sufficient for most measurements, which can be done in 2.4 seconds. With the position encoder (integrated with the motor in this unit) having 500 pulses per revolution, the maximum data-acquisition rate (analog-to-digital conversion rate) is 83,333 Hz (10,000/60 rev/sec×500 pulses/rev). This rate is within the maximum sampling rate of many data-acquisition cards, such as model #PCI-6032E available from National Instruments Corp. of Texas, USA.

More generally, embodiments of the present invention advantageously provide a continuously variable wavelength output by continuously spinning a CSWS device in one direction. As noted above, the CSWS device can be a combination of filter(s) and/or grating(s) where at least one of the filter(s) or grating(s) continuously spins to achieve wavelength scanning. Embodiments of the invention achieve fast measurements by practically removing the need to overcome inertial forces associated with acceleration, deceleration and settling down of the moving parts, e.g., a rotating filter/grating.

The use of a double-beam method reduces errors and drifts from most sources other than the detectors, e.g., photo-detector(s). One can design real-time analog filters and phase-locking techniques to isolate and extract certain spectral features of the sample and improve the SNR.

In other words, specifically enumerated, advantages of the present invention include the following:

1. Measurements are fast, because:
   a. There are no inertial effects to overcome, such as acceleration, deceleration and settling down of moving parts.
   b. Data processing can be done in real-time.
2. Fast measurements enable greater signal averaging in a given time
3. Embodiments of the invention reduce low frequency drifts through a feature-based modulation technique and through the speed of measurements.
4. Embodiments of the invention are relatively insensitive to mechanical positional error and vibrations.
5. Embodiments of the invention that use an interference filter provide high throughput relative to a grating based instrument due to the absence of an entrance slit or aperture. Compare the Thermo Oriel 56430 Narrow Band Filter with the Thermo Oriel 77250 ⅛ m Monochromator, both available from Thermo Oriel of Stamford, Conn., for isolation of a 20 nm bandwidth at 365 nm from an extended source. The monochromator has a standard 1200 1/mm grating.

The acceptance angle of this filter for the 20 nm bandwidth is approximately 15°. The corresponding solid angle is 0.21 sr. If the filter holder reduces the aperture to 0.9 inch (22.9 mm), the area is 4.1 cm$^2$ and $G_{fil}$=0.86 sr cm$^2$ where G is the optical extent. We must multiply this by the filter transmittance of 0.2 for comparison of throughout.

$G_{fil} T_{fil}$=0.17 sr cm$^2$

The acceptance angle of the 77250 Monochromator is 7.7° and the corresponding solid angle is 0.57 sr. For a 20 nm bandwidth, the slit width is 3.16 mm. As the usable slit height is 12 mm, the area is 0.38 cm$^2$, so:

$G_{mono}$=0.22 sr cm$^2$ and $G_{mono} T_{mono}$=0.007 sr cm$^2$

The optical filter isolating 20 nm from this extended source passes about 24 times as much light as the monochromator. If the light from the filter can be coupled to a detector, i.e., if the detector does not restrict the system, then the filter is much more efficient. This ratio does not apply to small asymmetrical sources such as the arcs of Oriel Arc Lamps. Each source should be examined individually.

6. Embodiments of the invention are simple and compact relative to conventional spectroscopic systems.
7. Embodiments of the invention are low-cost and do not need a high-precision drive system or a high-precision control system
8. Advantages 1 through 5 listed above provide the ability to achieve a higher SNR per unit time.

EXAMPLE

One can construct embodiments of the present invention according to FIGS. 1, 4 and 5 using the following components. One can use a 250W tungsten-halogen source such as model #LSH-T250 available from Jobin Yvon, Inc. of New Jersey, USA, as a broadband source (not shown in FIG. 1). One can use a narrow-band transmitting filter such as model #F12-2300-3 available from CVI Laser Corp. of New Mexico, USA as an interference filter portion of the CSWS device 20. One can use a BK7 glass (90% transmitted for the main sample, and 10% reflected for the reference sample), available from most optical component distributors and/or manufacturers such as CVI Laser Corp. of New Mexico, USA, as the beamsplitter 22. One can use a brush motor with integrated position encoder such as model #8324S005 available from Pittman of Pennsylvania, USA as the servo motor 44. One can use a 12A 80V brush motor amplifier such as model #12A8K available from Advanced Motion Controls of California, USA as the motor amplifier 56. Depending on the application, one can use 2-stage TE-cooled, extended InGaAs detectors such as model #IGA2.2-010-TE2-H available from Electro-Optical Systems, Inc. of Pennsylvania, USA as the first and second detectors 30, 32. In addition, one can use a 16-bit PCI-based A/D card such as model #PCI-6032E available from National Instruments Corp. of Texas, USA as an A/D converter (not shown) for receiving analog signals from analog circuitry 34 and for converting the analog signals to digital signals for processing by processor 36.

The mirror is conventional such as are available from most optical component distributors and/or manufacturers such as CVI Laser Corp. of New Mexico, USA.

The reference and sample cells are conventional such as can be purchased from Sepctrocell, Inc. of Pennsylvania, USA.

The position encoder is conventional. Many are motors, such as DC motor model #8324S005 available from Pittman of Pennsylvania, USA, come with an integrated position encoder.

Optics holder: can be an off-the-shelf component or a custom-machined component. Thorlabs, Inc. of New Jersey, USA is a company that sells off-the-shelf optics holders.

The F/V converter is conventional, such as the LM2907 or LM2917 F/V converters made by National Semiconductor Corp., and obtainable from various electronics distributors, such as Digi-Key Corp. of Minnesota, USA and Mouser Electronics, Inc. of Texas, USA.

Post-processing can be done in MATLAB from The MathWorks, Inc. of Massachusetts, USA.

With reference to FIG. 8A, experimental results using the above-described spinning-filter prototype include a feature-based modulated signal as a function of time (or as a function of encoder counts, as filter is rotating at a constant speed). V1 & V2 are voltage values of detector 1 and 2 respectively, which are proportional to the detected radiation power. V1 indicates the transmitted radiation power through pure water, and V2 indicates the transmitted radiation power through a water-glucose solution. With reference to FIG. 8B, processing the "raw" data shown in FIG. 8A produces the illustrated absorption spectrum. The post-processing performed to achieve FIG. 8B primarily involved data averaging.

Having thus described at least one illustrative embodiment of the invention, various alterations, modifications and improvements are contemplated by the invention including the following: Instead of mirror 24, one could use a variety of sets of optics (lenses and/or mirrors) to direct and/or focus the first and/or second subordinate beams on the sample cell and reference cells, respectively; systems according to the invention could collect EM radiation reflected from the target in contrast to collecting EM radiation transmitted through the target; embodiments of the invention are not limited to a double-beam configuration (for example, the invention contemplates a single beam configuration, i.e., a configuration without a reference cell). Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A spectroscopic system for collecting electromagnetic radiation from a target, the spectroscopic system comprising:
   a source of a primary beam of electromagnetic radiation;
   a continuously spinning wavelength-selecting device in the path of the primary beam, the device operative to pass only a restricted spectral band of the electromagnetic radiation to produce filtered radiation, the device comprising
   a motor;
   a filter coupled to the motor, the filter being adapted to spin about an axis that is substantially perpendicular to the primary beam; and
   a rotational velocity control in communication with the motor and operative to use a rotational velocity signal to control the rotational velocity of the filter;
   a beamsplitter in the path of the primary beam and operative to split the primary beam into a first subordinate beam and a second subordinate beam;
   a target cell in the path of the first subordinate beam, the target cell adapted to interact with a portion of the filtered radiation to produce filtered target radiation; and
   a reference cell in the path of the second subordinate beam adapted to interact with a portion of the filtered radiation to produce filtered reference radiation;
   a first detector in the path of the first subordinate beam and operative to detect the filtered target radiation and to produce detected target radiation information;
   a second detector in the path of the second subordinate beam and operative to detect the filtered reference radiation and to produce detected reference radiation information; and
   a processing device in communication with the first and second detectors and operative to process the detected target radiation information and the detected reference radiation information and to produce processed target information.

2. A spectroscopic system for collecting electromagnetic radiation from a target, the spectroscopic system having at least one beam comprising a primary beam of electromagnetic radiation that interacts with the target, the spectroscopic system comprising:

a wavelength-selecting device including a filter configured to spin continuously about an axis that is substantially perpendicular to the primary beam for more than one rotation in the path of the at least one beam and operative to filter the radiation with regard to wavelength to produce filtered radiation;

a motor, the motor being coupled to the filter so as to be able to spin the filter about the axis that is substantially perpendicular to the primary beam;

a rotational velocity control coupled to the motor and operative to use a rotational velocity signal to control the rotational velocity of the filter; and at least one detector in the path of the at least one beam for detecting the filtered radiation.

3. The system of claim 2, wherein the system further comprises a position encoder coupled to the device and operative to determine the rotational position of the filter.

4. The system of claim 3 wherein the encoder is operative to determine the rotational speed of the filter and to provide digital pulses with a frequency proportional to the rotational speed of the filter and wherein the system further comprises a frequency-to-voltage (F/V) converter in communication with the encoder and operative to receive the digital pulses and to provide a feedback voltage proportional to the frequency of the digital pulses; and a voltage comparison circuit in communication with the F/V converter and operative to receive a command voltage and the feedback voltage, to compare the command voltage and the feedback voltage and to regulate the rotational speed of the motor based on the comparison.

5. The system of claim 2, wherein an optics holder couples the filter to the motor.

6. A spectroscopic system for collecting electromagnetic radiation from a target, the spectroscopic system having at least one beam comprising a primary beam of electromagnetic radiation that interacts with the target, the spectroscopic system comprising:

a wavelength-selecting device including a filter configured to spin continuously about an axis that is substantially perpendicular to the primary beam for more than one rotation in the path of the at least one beam and operative to filter the radiation with regard to wavelength to produce filtered radiation, wherein the filter is a transmitting interference filter;

a motor, the motor being coupled to the filter so as to be able to spin the filter about the axis that is substantially perpendicular to the primary beam; and at least one detector in the path of the at least one beam for detecting the filtered radiation.

7. The system of claim 2, wherein the target reflects the primary beam.

8. The system of claim 2, wherein the target transmits the primary beam.

9. The system of claim 2, wherein the device is positioned to receive the primary beam before it interacts with the target.

10. The system of claim 2, wherein the device is positioned to receive the primary beam after it interacts with the target.

11. The system of claim 2, wherein the at least one beam further comprises a first subordinate beam and a second subordinate beam and wherein the system further comprises:

a beamsplitter in the path of the primary beam operative to split the primary beam into the first subordinate beam and the second subordinate beam;

a target cell in the path of the first subordinate beam, the target cell adapted to interact with a portion of the filtered radiation to produce filtered target radiation; and a reference cell in the path of the second subordinate beam adapted to interact with a portion of the filtered radiation to produce filtered reference radiation.

12. The system of claim 11 wherein the at least one detector comprises:

a first detector in the path of the first subordinate beam and operative to detect the filtered target radiation and to produce detected target radiation information; and a second detector in the path of the second subordinate beam and operative to detect the filtered reference radiation and to produce detected reference radiation information.

13. The system of claim 12 wherein the system further comprises a processing device in communication with the first and second detectors and operative to process the detected target radiation information and the detected reference radiation information and to produce processed target information.

14. A spectroscopic system for collecting electromagnetic radiation from a target, the spectroscopic system having at least one beam comprising a primary beam of electromagnetic radiation that interacts with the target, the spectroscopic system comprising:

a wavelength-selecting device including a filter configured to spin continuously about an axis that is substantially perpendicular to the primary beam for more than one rotation in the path of the at least one beam and operative to filter the radiation with regard to wavelength to produce filtered radiation, wherein the filter comprises a plurality of interference elements; and at least one detector in the path of the at least one beam for detecting the filtered radiation.

15. The system of claim 14 wherein the plurality of interference elements comprises a plurality of interference filters.

16. The system of claim 14 wherein the plurality of interference elements comprises at least one interference filter and at least one interference grating.

17. A spectroscopic method for collecting electromagnetic radiation from a target that interacts with at least one beam including a primary beam of electromagnetic radiation, the method comprising:

filtering the at least one beam using a wavelength-selecting device that includes a transmitting interference filter that spins continuously about an axis that is substantially perpendicular to the primary beam for more than one rotation to produce filtered radiation and a motor that is coupled with the filter, the motor spinning the filter about the axis that is substantially perpendicular to the primary beam; and detecting the filtered radiation.

18. The method of claim 17, wherein spinning the filter about the axis that is substantially perpendicular to the primary beam comprises using a rotational velocity control to control the rotational velocity of the filter.

19. The method of claim 17, wherein spinning the filter about the axis that is substantially perpendicular to the primary beam comprises using a position encoder to determine the rotational position of the filter.

20. The method of claim 19 wherein spinning the filter comprises using the encoder to determine the rotational speed of the filter and to provide digital pulses with a frequency proportional to the rotational speed of the filter and wherein the method further comprises provide a frequency-to-voltage (F/V) converter in communication with the encoder;

using the F/V converter to receive the digital pulses and to provide a feedback voltage proportional to the frequency of the digital pulses;

providing a voltage comparison circuit in communication with the F/V converter; and using the voltage comparison circuit to receive a command voltage and the feedback voltage, to compare the command voltage and the feedback voltage and to regulate the rotational speed of the motor based on the comparison.

21. The method of claim 17, wherein the target reflects the primary beam.

22. The method of claim 17, wherein the target transmits the primary beam.

23. The method of claim 17, wherein the method further comprises filtering the primary beam before it interacts with the target.

24. The method of claim 17, wherein the method further comprises filtering the primary beam after it interacts with the target.

25. The method of claim 17, wherein the at least one beam further comprises a first subordinate beam and a second subordinate beam and wherein the system further comprises:

splitting the primary beam into the first subordinate beam and the second subordinate beam using a beamsplitter;

directing the first subordinate beam to interact with a target cell to produce filtered target radiation; and directing the second subordinate beam to interact with a reference cell to produce filtered reference radiation.

26. The method of claim 25 wherein detecting the filtered radiation comprises:

detecting the filtered target radiation; and detecting the filtered reference radiation.

27. A spectroscopic method for collecting electromagnetic radiation from a target that interacts with at least one beam including a primary beam of electromagnetic radiation, the method comprising:

filtering the at least one beam using a wavelength-selecting device that includes a plurality of interference filters that spin continuously about an axis that is substantially perpendicular to the primary beam for more than one rotation to produce filtered radiation and a motor that is coupled with the filters, the motor spinning the filters about the axis that is substantially perpendicular to the primary beam; and detecting the filtered radiation.

28. The method of claims 17, wherein the device further comprises a position encoder coupled to the motor and operative to determine the position of the filter and wherein the method further comprises using the position encoder to clock data acquisition.

* * * * *